United States Patent [19]

Yasuda et al.

[11] Patent Number: 5,130,314
[45] Date of Patent: Jul. 14, 1992

[54] CARBOSTYRIL SUBSTITUTED PYRIDAZINONES

[75] Inventors: Kikuo Yasuda, Yokohama; Kenyu Shibata, Inagi; Nobuyoshi Minami, Yokohama; Toshimi Seki, Kawasaki; Masafumi Shiraiwa, Kawasaki; Tomio Nakao, Inagi; Katsuhiko Miyasaka, Atsugi; Tsutomu Ishimori, Kawasaki; Kotaro Gotanda, Kawasaki; Takako Sasaki, Tokyo, all of Japan

[73] Assignee: Teikoku Hormone Mfg. Co., Ltd., Tokyo, Japan

[21] Appl. No.: 770,287

[22] Filed: Sep. 27, 1991

Related U.S. Application Data

[62] Division of Ser. No. 539,741, Jun. 18, 1990, Pat. No. 5,082,844.

[30] Foreign Application Priority Data

Jun. 19, 1989 [JP] Japan .................................. 1-154452
Jun. 11, 1990 [JP] Japan .................................. 2-149803

[51] Int. Cl.$^5$ ............................................. A61K 31/50
[52] U.S. Cl. ...................................... 514/253; 544/238
[58] Field of Search ............................. 514/253, 238

[56] References Cited

U.S. PATENT DOCUMENTS

| | | | |
|---|---|---|---|
| 4,027,027 | 5/1980 | Jaeggi | 544/239 |
| 4,217,350 | 8/1980 | Eichenberger | 514/252 |
| 4,532,239 | 7/1985 | Raabe et al. | 544/239 |
| 4,599,333 | 7/1986 | Yasuda et al. | 544/239 |
| 4,608,383 | 8/1986 | Wiedemann et al. | 514/247 |
| 4,810,712 | 3/1989 | Cohnen et al. | 514/312 |
| 4,843,072 | 6/1989 | Yasuda et al. | 544/239 |
| 4,894,219 | 1/1990 | Baker | 514/312 |
| 4,914,094 | 4/1990 | Oshiro | 514/247 |
| 4,935,414 | 1/1990 | Stenzel | 514/253 |

FOREIGN PATENT DOCUMENTS

| | | |
|---|---|---|
| 0259835 | 3/1988 | European Pat. Off. |
| 0404050 | 12/1990 | European Pat. Off. ............ 544/238 |
| 0146570 | 9/1983 | Japan ................................. 544/239 |

OTHER PUBLICATIONS

Chem. Abstr vol. 112 entry 198402(e) (1990).
Slater et al., Journal Med. Chem., vol. 31 pp. 345-347 (1988).

Primary Examiner—Donald G. Daus
Attorney, Agent, or Firm—Wenderoth, Lind & Ponack

[57] ABSTRACT

A pyridazinone compound represented by the general formula

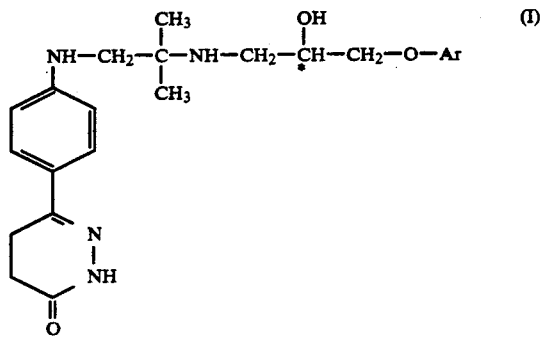

wherein Ar is

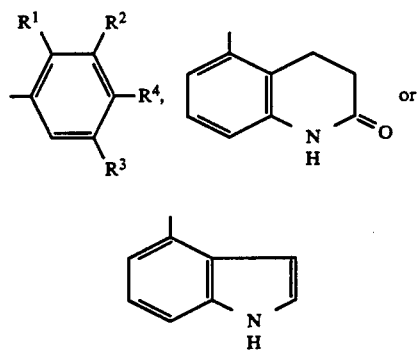

in which $R^1$, $R^2$ and $R^3$ may be identical or different, and each represents a hydrogen atom, a lower alkyl group, a trifluoromethyl group, a halogen atom, a cyano group or a nitro group, and $R^4$ represents a hydrogen atom, a lower alkoxy group, or a lower alkyl group substituted by a lower alkoxy group or a carbamoyl group, and C* is an assymmetric carbon atom, or a salt thereof. This compound is useful for the treatment of diseases of the circulatory system.

3 Claims, No Drawings

CARBOSTYRIL SUBSTITUTED PYRIDAZINONES

This application is a division of application Ser. No. 07/539,741, filed Jun. 18, 1990, U.S. Pat. No. 5,082,844.

This invention relates to a novel pyridazinone derivatives, more specifically, to a pyridazinone compound represented by the following formula

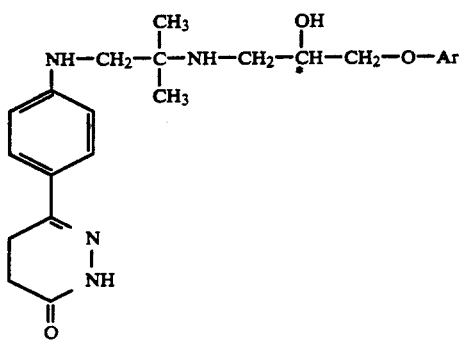

wherein Ar represents a group of the formula

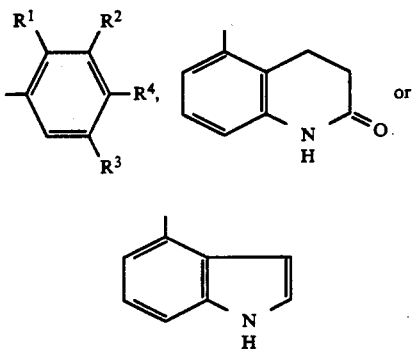

in which $R^1$, $R^2$ and $R^3$ may be identical or different and each represents a hydrogen atom, a lower alkyl group, a trifluoromethyl group, a halogen atom, a cyano group or a nitro group, $R^4$ represents a hydrogen atom or a lower alkyl group substituted by a carbamoyl group or a lower alkoxy group, and C* represents an asymmetric carbon atom.

or a salt thereof, and to a hypotensive agent comprising a pyridazinone compound of formula (I) or a pharmaceutically acceptable salt thereof as an active ingredient.

Many compounds having a hypotensive action have been proposed. Vasodilators which have been much used as hypotensive agents generally have an accurate hypotensive action, but have the defect of involving tachycardia. On the other hand, sympathetic nerve beta-receptor blocking (to be referred to as beta-blocking) agents are also used as hypotensive agents, and have the advantage of not involving tachycardia. But their hypotensive action is slow-acting and weak. Hence in the treatment of hypertensive patients, vasodilators and beta-blocking agents, when administered alone, cannot be expected to give a sufficient effect. In the conventional clinical treatment, it has often been the practice to administer both vasodilators and beta-blocking agents at the same time. This simultaneous administration is troublesome to the patients, and is not a desirable form of drug administration.

Accordingly, it is desired to develop a hypotensive agent having the advantages of a vasodilator and the advantages of a beta-blocking agent. Recently, several publications suggested hypotensive agents which have both a beta-blocking action and a vasodilating action (for example, U.S. Pat. No. 4,053,601 and Japanese Laid-Open Patent Publication No. 32489/1979). These publications show little data which will substantiate these actions. Alternatively, it was determined that the compounds have a beta-blocking action and a vasodilating action at the same time, but the activity actually shown was very weak.

Previously, the present inventors found, and proposed, in European Patent 259835 and U.S. Pat. No. 4,543,072, that pyridazinone derivatives of the following formula

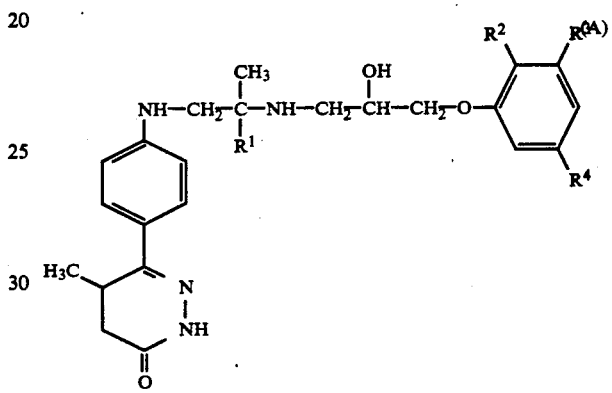

R1 represents a hydrogen atom or a methyl group, either one of R2, R3 and R4 represents a hydrogen atom and the remaining two represent a lower alkyl group, a trifluoromethyl group, a halogen atom, a cyano group, or a nitro group, or salts thereof simultaneously have an excellent beta-blocking action and an excellent vasodilating action, and are very useful therapeutically as a long-lasting hypotensive agent free from tachycardia.

The present inventors furthered their work, and have now found that compounds of formula (A) in which the pyridazinone moiety does not have a methyl group have a well-balanced combination of beta-blocking and vasodilating actions and very little tachycardia as a side-effect.

When the asymmetric carbon atom represented by C* in compounds of general formula (1) provided by this invention has an S-configuration, the compounds of formula (1) are especially useful as hypotensive agents which cause little tachycardia and have little effects on the heart.

The term "lower" used to qualify a group or a compound means that a group or a compound so qualified has not more than 5, preferably not more than 3, carbon atoms.

The "lower alkyl group" may be linear or branched, and includes, for example, methyl, ethyl, n-propyl, iso-propyl, n- iso-, sec- or tert-butyl group. Methyl and ethyl groups are especially preferred.

The "lower alkoxy group" are lower alkyloxy groups in which the lower alkyl moiety has the above meaning, and examples include methoxy, ethoxy, n-propoxy, iso-propoxy, n-butoxy, and tert-butoxy groups. Specific examples of the lower alkyl group substituted by a lower alkoxy group or a carbamoyl group include 2-methoxyethyl, 2-ethoxyethyl, 3-methoxypropyl, tert-butoxymethyl carbamoyl methyl and 2-carbamoylethyl groups.

(1) Compounds of formula (I) in which Ar represents

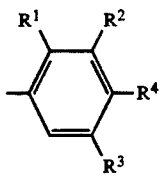

in which $R^1$ represents a hydrogen atom or a cyano group, $R^2$ and $R^4$ represent a hydrogen atom, and $R^3$ represents a halogen atom, or $R^4$ represents a loweralkyl group substituted by a lower alkoxy group or a carbamoyl group, and $R^1$, $R^2$ and $R^3$ are hydrogen atoms, and (2) Compounds of formula (1) in which Ar represents

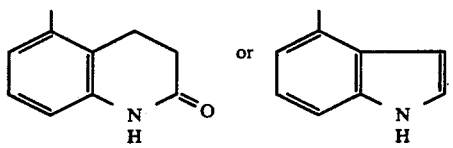

are a preferred group of compounds formula (I).

Specific examples of the compound of formula (I) provided by this invention include:

(2S)-6-[4-[2-[2-[3-(5-chloro-2-cyanophenoxy)-hydroxypropylamino]-2-methylpropylamino]phenyl]-4,5-dihydro-3(2H)-pyridazinone, (2S)-6-[4-[2-[3-(2,5-dichlorophenoxy)-2-hydroxy-propylamino]2-methylpropylamino]phenyl]-4,5-dihydro-3(2H)-pyridazinone, 6-[4-[2-[3-(2,3-dichlorophenoxy)-2-hydroxy-propylamino]-2-methylpropylamino]phenyl]-4,5-dihydro-(2H)-pyridazinone, (2S)-6-[4-[2-[3-(3,5-dimethylphenoxy)-2-hydroxy-propylamino]phenyl]-4,5-dihydro-3(2H)-pyridazinone, (2S)-6-[4-[2-[3-(5-chloro-2-methylphenoxy)-2-hydroxypropylamino]-2-methylpropylamino]-phenyl]4,5-dihydro-3(2H)-pyridazinone, (2S)-6-[4-[2-[3-(2-chloro-5-trifluoromethylphenoxy)-2-hydroxypropylamino]-2-methylpropylamino]-phenyl]-4,5-dihydro-3(2H)-pyridazinone, (2S)-6-[4-[2-[3-(2-chloro-5-cyanophenoxy)-2-hydroxypropylamino]-2-methylpropylamino]phenyl]-4,5-dihydro-3(2H)-pyridazinone, 6-[4-[2-[3-(2-chloro-5-nitrophenoxy)-2-hydroxy-3(2H)-pyridazinone, 6-[4-[2-[3-(3-chloro-2-cyanophenoxy)-2-hydroxy-propylamino]-2-methylpropylamino]phenyl]-4,5-dihydro-3(2H)-pyridazinone, 6-[4-[2-[3-(2-methyl-3-nitrophenoxy)-2-hydroxy-3(2H)-pyridazinone, (2S)-6-[4-[2-[3-(2-chloro-5-methylphenoxy)-2-hydroxypropylamino]-2-methylpropylamino]phenyl]-4,5-dihydro-3(2H)-pyridazinone, 6-[4-[2-[3-(5-ethyl-2-methylphenoxy)-2-hydroxy-propylamino]-2-methylpropylamino]phenyl]-4,5-dihydro-3(2H)-pyridazinone, 6-[4-[2-[3-(5-bromo-2-ethylphenoxy)-2-hydroxy-propylamino]-2-methylpropylamino]phenyl]-4,5-dihydro-3(2H)-pyridazinone, (2S)-6-[4-[2-[3-(5-chloro-2-ethylphenoxy)-2-hydroxypropylamino]-2-methylpropylamino]phenyl]-4,5-dihydro-3(2H)-pyridazinone, 6-[4-[2-[3-(2-bromo-5-methylphenoxy)-2-hydroxy-propylamino]-2-methylpropylamino]phenyl]-4,5-dihydro-3(2H)-pyridazinone, 6-[4-[2-[3-(2-bromo-5-nitrophenoxy)-2-hydroxy-propylamino]-2-methylpropylamino]phenyl]-4,5-dihydro-3(2H)-pyridazinone, 6-[4-[2-[3-(5-fluoro-2-methylphenoxy)-2-hydroxy-propylamino]-2-methylpropylamino]phenyl]-4,5-dihydro-3(2H)-pyridazinone, 6-[4-[2-[3-(5-fluoro-2-nitrophenoxy)-2-hydroxy-propylamino]-2-methylpropylamino]phenyl]-4,5-dihydro-3(2H)-pyridazinone, 6-[4-[2-[3-(2-methyl-5-nitrophenoxy)-2-hydroxy-propylamino]-2-methylpropylamino]phenyl]-4,5-dihydro-3(2H)-pyridazinone, 6-[4-[2-[3-(2-ethyl-3-methylphenoxy)-2-hydroxy-propylamino]-2-methylpropylamino]phenyl]-4,5-dihydro-3(2H)-pyrimidazinone, 6-[4-[2-[3-(3-chloro-5-methylphenoxy)-2-hydroxy-propylamino]-2-methylpropylamino]phenyl]-4,5-dihydro-3(2H)-pyridazinone, (2S)-6-[4-[2-[3-(2-chloro-3-nitrophenoxy)-2-hydroxy-propylamino]-2-methylpropylamino]phenyl]-4,5-dihydro-3(2H)-pyridazinone, 6-[4-[2-[3-(5-methyl-2-nitrophenoxy)-2-hydroxy-propylamino-2-methylpropylamino]phenyl]-4,5-dihydro-3(2H)-pyridazinone, 6-[4-[2-[3-(5-chloro-2-cyanophenoxy)-2-hydroxy-propylamino]-2-methylpropylamino]phenyl]-4,5-dihydro-3(2H)-pyridazinone, 6-[4-[2-[3-(2,5-dichlorophenoxy)-2-hydroxy-propylamino]-2-methylpropylamino]phenyl]-4,5-dihydro-3(2H)-pyridazinone, 6-[4-[2-[3-(2-cyanophenoxy)-2-hydroxypropyl-amino]-2-methylpropylamino]phenoxy]-4,5-dihydro-3(2H)-pyridazinone, 6-[4-[2-[3-(4-carbamoylmethylphenoxy)-2-hydroxy-propylamino]-2-methylpropylamino]phenyl]-4,5-dihydro-3(2H)-pyridazinone, 6-[4-[2-(3-phenoxy-2-hydroxypropylamino)-2-methylpropylamino]phenyl]-4,5-dihydro-3(2H)-pyridazinone, 6-[4-[2-[3-[4-(2-methoxyethyl)phenoxy]-2-hydroxy-propylamino]-2-methylpropylamino]phenyl]-4,5-dihydro-3(2H)-pyridazinone, 6-[4-[2-[3-(3,4-dihydrocarbostyril-5-yloxy)-2-hydroxypropylamino]-2-methylpropylamino]phenyl]-3,4-dihydro-3(2H)-pyridazinone, and 6-[4-[2-[3-(indol-4-yloxy)-2-hydroxypropyl-amino]-2-methylpropylamino]phenyl]-4,5-dihydro-3(2H)-pyridazinone.

The present invention also provide acid addition salts of the pyridazinone compounds of formula (I). The acid addition salts of the compounds of formula (I) are, for example, inorganic acid salts the compounds of formula (I), such as the hydrochlorides, hydrobromides, sulfates, nitrates, and phosphates, and their organic acid salts such as the acetates, propionates, citrates, lactates and tartrates. Of these, pharmaceutically acceptable acid addition salts are advantageously used.

According to this invention, the pyridazinone derivatives of formula (I) may be produced by the reaction route shown in reaction scheme A.

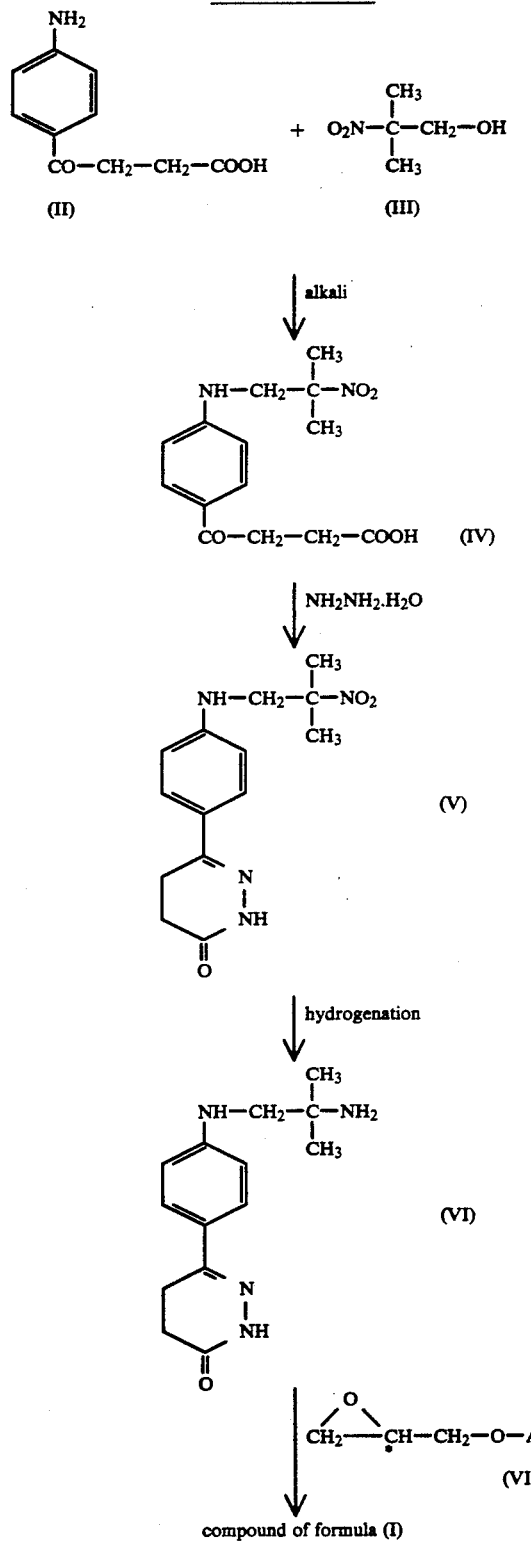

In the reaction scheme A, the reaction of the compound of formula (II) or its salt with compound of formula (III) may be carried out by dehydrocondensation generally in a suitable inert reaction medium, for example, water, an alcohol such as methanol or ethanol, a mixed solvent such as water-methanol. Usually the condensation is carried out under neutral or weakly alkaline conditions. To maintain the reaction system under these conditions, it is desirable to add an alkali, such as sodium hydroxide, potassium hydroxide, sodium carbonate, potassium carbonate or sodium hydrogen carbonate, to the reaction system. The dehydrocondensation reaction may proceed even in the absence of a catalyst. Generally, it is advantageous to perform the reaction in the presence of a reaction promoter such as benzyl triethyl ammonium chloride, benzyl trimethyl ammonium chloride, tetrabutyl ammonium bromide. The amount of the reaction promoter is not especially limited. Usually, the suitable amount of the reaction promoter is 0.01 mole to 0.02 mole per mole of the compound of formula (II).

The compound of formula (II) may be used in a free form. Generally, it is easy and convenient to handle if it is in the form of an acid addition salt, such as a hydrochloride.

The proportion of the compound of formula (III) to the compound of formula (II) is not strictly and can be changed according to the reaction conditions. Generally, the proportion of the compound of formula (III) is suitably 1 to 5 moles, preferably 1 to 2 moles, per mole of the compound of formula (II).

The reaction temperature in the dehydrocondensation is about 50° C. to the refluxing temperature of the reaction mixture, preferably the refluxing temperature. Thus, a compound of (IV) is formed. Since this compound precipitates as crystals when an acid is added to the reaction mixture, it is separated by such means as filtration, and then reacted with hydrazine hydrate usually in an aqueous medium to cyclize it. This reaction is carried out generally at a temperature of about 60° to about 100° C., preferably 80° to 100° C. The amount of the hydrazine hydrate is not particularly limited. Generally, the suitable amount of the hydrazine hydrate is 1 to 10 moles, preferably 2 to 5 moles, per mole of the compound of formula (IV).

The compound of formula (V) obtained by the cyclization reaction can then be changed to the compound of formula (VI) by hydrogenation. This hydrogenation can be carried out in a suitable inert medium such as an alcohol (e.g., methanol or ethanol), dimethylformamide or dimethylacetamide by contacting the compound of formula (VI) with hydrogen in the presence of a hydrogenation catalyst such as Raney nickel, palladium, or palladiumcarbon. The pressure of hydrogen is generally 1 to 100 atmospheres, preferably 1 to 10 atmospheres. The suitable reaction temperature is from room temperature to 70° C.

The compound of formula (VI) is then reacted with a compound of formula (VII) to give the desired compound of formula (I). The reaction of the compound of formula (VI) with the compound of formula (VII) may be carried out in the absence of a solvent. Generally, it may be carried out in an inert medium, for example, an alcohol such as methanol, ethanol, propanol or butanol, an ether such as diethyl ether, dioxane, or tetrahydrofuran, an aromatic hydrocarbon such as benzene, toluene or xylene, or a halogenated hydrocarbon such as dichloromethane, chloroform or tetrachloroethane. The reaction temperature is not strictly limited. Generally, it is about 20° C. to the refluxing temperature of the reaction mixture, preferably from 50° to 100° C. The amount of the compound of formula (VII) relative to the compound of formula (VI) can be varied over a wide range. Generally, it is advantageous to use 0.1 to 20 moles, preferably 0.2 to 5 moles, of the compound of formula (VII) per mole of the compound of formula (VI).

As a result, the desired compound of formula (I) may be obtained in good yields.

The recovery and purification of the compound of formula (I) from the reaction mixture may be carried out by known methods, such as extraction, column chromatography, thin-layer chromatography, and recrystallization. The epoxy compound of formula (VII) may be easily produced by reacting an epihalohydrin with the phenol derivative of formula (VIII) in accordance with the following reaction scheme B.

Reaction scheme B

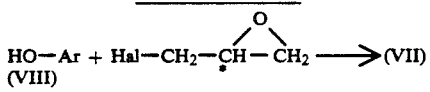

wherein Hal represents a halogen atom, and Ar and C* are as defined above.

The pyridazinone compound of formula (I) produced as above, may be, as required, treated, by a known method, with an inorganic acid such as hydrochloric acid, hydrobromic acid, sulfuric acid, nitric acid or phosphoric acid, or an organic acid such as acetic acid, propionic acid, oxalic acid, maleic acid, citric acid, lactic acid, tartric acid or methanesulfonic acid to convert it to the corresponding salt.

The pydirazinone compound of formula (I) provided by this invention is therapeutically very good as a long-lasting hypotensive agent which has a beta-blocking action and a vasodilating action in a well-balanced combination and does not cause tachycardia.

The following animal experiments will demonstrate that the compound of formula (I) develop excellent beta-blocking action and vasodilating action (hypotensive activity) without causing tachycardia.

Compounds of the invention

A 6-[4-[2-[3-(5-chloro-2-cyanophenoxy)-2-hydroxypropylamino]-2-methylpropylamino]phenyl]-4,5-dihydro-3(2H)-pyridazinone B: (2S)-6-[4-[2-[3-(5-chloro-2-cyanophenoxy)-2-(hydroxypropylamino]-2-methylpropylamino]phenyl]-4,5-dihydro-3(2H)-pyridazinone C: 6-[2-[3-(2-cyanophenoxy)-2-hydroxypropylamino]-2-methylpropylamino]phenyl]-4,5-dihydro-3(2H)-pyridazinone D: 6-[4-[2-[3-(3,4-dihydrocarbostyril-5-yloxy)-2-hydroxypropylamino]-2-methylpropylamino]phenyl]-4,5-dihydro-3(2H)-pyridazinone E: 6-[4-[2-[3-indol-4-yloxy)-2-hydroxypropyl-amionmo]phenyl]-4,5-dihydro-3(2H)-pyridazinone F: 6-[4-[2-(3-phenoxy-2-hydroxypropylamino)-2-methylpropylamino]phenyl]-4,5-dihydro-3(2H)-pyridazinone G: 6-[4-[2-[3-(4-carbamoylmethylphenoxy)-2-hydroxypropylamino]-2-methylpropylamino]phenyl]-4,5-dihydro-3(2H)-pyridazinone H: 6-[4-[2-[3-[4-(2-methoxyethyl)phenoxy]-2-hydroxypropylamino]-2-methylpropylamino]phenyl]-4,5-dihydro-3(2H)-pyrydazinone Control compounds I: 6-[4-[2-[3-(5-chloro-2-cyanophenoxy)-2-hydroxypropylamino]-2-methylpropylamino]phenyl]-5-methyl-4,5-dihydro-3(2H)-pyridazinone J: 1-[(1-methylethyl)amino]-3-(1-naphthalenyl-oxy)-2-propanol (propronolol)

Testing Methods (1) Measurement of the beta-blocking action

Pentobarbital(60 mg/kg, i.p.)-anaethetized rats (Wistar, male, body weight 350–420g), four per group, were used, and the blood pressure was measured by a pressure transducer connected via cannula inserted into the femoral artery. The heart rate was calculated from the blood pressure pulsating wave. Isoprenalin (0.1 microgram/kg i.v) was administered, and immediately after, the heart rate was measured and recorded. The measured value of the increase in heart rate at this time was $H_1$. The test compound was suspended in 0.2% Tween 80 - physiological saline, and the resulting suspension was administered through a cannula inserted into the femoral vein of the rat. Four minutes later, isoprenalin (0.1 microgram/kg i.v.) was again administered. The reading of the increase in heart rate at that time was $H_2$. From these measured values, the percent inhibition of the heart rate was calculated from the following equation.

$$\text{Percent inhibition of the heart rate (\%)} = 100 - \frac{H_2}{H_1} \times 100$$

By increasing the dose of the test compound cumulatively, the dose-reaction curve was prepared. The dose of the test compound was determined from the curve when the percent inhibition of the tachycardia became 50%. The dose was compared with propranolol, and the results are shown in Table 1.

(2) Measurement of the hypotensive action

Pentobarbital (60 mg/kg, i.p.)-anaesthetized rats (Wister, male, body weight 350–420 g) 4 per group were used, and the blood pressure was measured by a pressure transducer connected via a cannula inserted in the femoral artery. The test compound was suspended in 0.2% Tween 80—physiological saline, and the suspension was administered intravenously in a dose of 1 mg/kg. The blood pressure was measured and recorded before and 20 min. after the administration, and the difference was calculated to determine the hypotensive action of the test compound.

The results are also shown in Table 1.

(3) Measurement of the hypotensive action and the heart rate.

From the results in (2), compound A is considered to have a well-balanced combination of beta-blocking action and vasodilating action in comparison with the control compound (I). The hypotensive action and the heart rate change of compound A were measured by the following methods.

To spontaneously hypertensive rats (male, 14 to 17 weeks old), 9 per group, the test compound dissolved or suspended in 1% gum arabic-distilled water was orally administered. The blood pressure and the heart rate were measured before the administration and 3 hours after the administration by an indirect method. The difference between both was calculated, and the hypotensive action (the dose which lowered the blood pressure by 30 mmHg, and change in heart rate (the change in heart rate at the dose which lowered the blood pressure by 30 mmHg), were determined. The results are shown in Table 2.

TABLE 1

| Compound | Beta-blocking action (propranolol = 1) | Hypotensive action (1 mg/kg, iv, mmHg) |
|---|---|---|
| A | 0.5 | 15 |
| B | 1 | 20 |
| C | 4 | 30 |
| D | 5 | 15 |
| E | 2 | 15 |
| F | 4 | 15 |
| G | 0.5 | 15 |
| H | 0.5 | 20 |
| I | 0.5 | 35 |
| J | 1 | 6 |

(*)Beta-blocking actions of compounds G and H are heart selective.

TABLE 2

| Compound | Beta-blocking action (microgram/kg, i.v.) | Hypotensive action (mg/kg p.o.) | Heart rate (per min.) |
|---|---|---|---|
| A | 64 | 5.8 | 26 lowered |
| I | 65 | 1.1 | 19 elevated |

Since the compounds of formula (I) provided by this invention have a well-balanced combination of beta-blocking action and vasodilating action, they may be administered orally or parenterally (for example by intramuscular injection, intravenous injection, subcutaneous administration, intrarectal administration or sublingual administration) to man and other warm-blooded animals for the treatment of diseases of the cardiovascular system such as hypertension, heart failure, angina pectoris, cerebral vascular insufficiency, and arrhythmia.

The compound of this invention may be formulated into various forms suitable for oral and parenteral administration. For example, the compound of this invention, may be formulated by using usually used nontoxic vehicles, binders, lubricants, disintegrants, antiseptics, isotonizing agents, stabilizers, dispersants, antioxidants, coloring agents, flavoring agents, and buffers. Depending upon its uses, such drug may be prepared into a solid form (such as tablets, hard capsules, soft capsules, granules, powers, pellets, pills and trouches), a semisolid form (such as suppositories) and a liquid form (such as an injectable, an emulsion, a suspension and a syrup).

Examples of non-toxic additives that can be used in this invention include starch, gelatin, glucose, lactose, fructose, maltose, magnesium carbonate, talc, magnesium stearate, methyl cellulose, carboxymethyl cellulose or its salts, gum arabic, polyethylene glycol, alkyl p-hydroxybenzoates, syrup, ethanol, propylene glycol, vaseline, carbowax, glycerol, sodium chloride, sodium sulfite, sodium phosphate and citric acid.

The above drug may also contain a therapeutically useful drug.

The amount of the compound of the invention in the drug varies according to its form. Desirably, it is 5 to 100% by weight for the solid and semisolid forms, and 0.1 to 10% by weight for the liquid form.

The dose of the compound of this invention may be widely varied depending upon the type of the warm-blooded animal to which it is administered, the severity of the condition, or the diagnosis of the physician. Generally, it may be 0.02 to 30 mg/kg, preferably 0.05 to 10 mg/kg, per day. It may be administered in doses which are less than the lower limit specified above or larger than the above-specified upper limit depending upon the severity of the patient's condition or the physician's diagnosis. The above dose may be administered once daily or in several divided dosages per day.

The following examples further specifically illustrate the present invention.

In the following Examples, all temperatures are ° C., and NMR measurement was made using tetramethylsilane as an internal standard.

EXAMPLE 1

(2S)-6-[4-[2-[3-(5-chloro-2-cyanophenoxy)-2-hydroxypropylamiono]-2-methylpropylamino]phenyl]-4,5-dihydro-3(2H)-pyridazinone:

(1) Production of 3-[4-(2-methyl-2-nitropropylamino)benzoyl]benzoyl]propionic acid:

A mixed solution containing 46 g of 3-(p-aminobenzoyl)propionic acid hydrochloride, 25 g of 2-methyl-2-nitro-1-propanol, 1 g of benzyl triethyl ammonium chloride, 17 g of sodium hydroxide and 40 ml of water was heated under reflux for 6 hours. Then, 12 g of 2-methyl-2-nitro-1-propanol was added, and the mixture was further heated under reflux for 18 hours. Then 20% HCl was added. The solution was acidified (pH 2). The crystals which precipitated were collected by filtration. The crystals were washed with water and recrystallized from tetrahydrofuran to give 51.6 g of 3-[4-(2-methyl-2-nitropropylamino)benzoyl]propionic acid.

m.p. 198.0°–200° C.

IR KBr cm$^{-1}$; 3368 1704, 1658, 1532, 1372, 1332, 1236, 1178

NMR (DMSO —d$_6$) δ; 1.58(6H, s), 2.35–2.60, (2H, m), 2.90–3.20(2H, m), 3.67(2H, d, J=7.1Hz), 6.60(1H, broad), 6.74(2H, d, J=8.7Hz), 7.71(2H, d, J=8.7Hz).

(2) Production of 6-[4-(2-methyl-2-nitropropylamino)phenyl]-4,5-dihydro-3(2H)-pyridazinone:

A solution composed of 42 g of 3-[4-(2-methyl-2-nitropropylamino)benzoyl]benzoyl]propionic acid obtained in (1) above, 22 g of 100% hydrazine hydrate and 600 ml of water was heated on a steam bath for 3 hours. The crystals that precipitated were collected by filtration, washed and dried to give 37.5 g of 6-[4-(2-methyl-2-nitropropylamino)phenyl]-4,5-dihydro-3(2H)-pyridazinone.

m.p 220°–222° C.

IR KBr cm$^{-1}$; 3352, 1650, 1614, 1356,

NMR (DMSO—d$_6$) δ; 1.60(6H, s), 2.20–2.50, (2H, m), 2.60–2.95(2H, m), 3.61(2H, d, J=7.0Hz), 6.10(1H, broad), 6.69(2H, d, J=8.7Hz), 7.44(2H, d, J=8.7Hz), 10.59(1H, s).

(3) Production of 6-[4-(2-amino-2-methylpropylamino)phenyl]-4,5-dihydro-3(2H)-pyridazinone:

36 g of 6-[4-(2-methyl-2-nitropropylamino)-phenyl]-4,5-dihydro-3(2H)-pyridazinone obtained in (2) above was dissolved in 300 ml of dimethylformamide. Twenty milliliters of Raney nickel was added to the solution, and the solution was heated to 45° to 50° C. and the hydrogenation was carried out at atmospheric pressure. After the end of the reaction, the catalyst was separated by filtration, and the dimethylformamide was evaporated under reduced pressure. The remaining crystals were recrystallized from methanol to give 26.9 g of 6-[4-(2-amino-2-methylpropylamino)phenyl]-4,5-dihydro-3(2H)-pyridazinone.

m.p. 190.0°–191.5° C.

IR KBr cm$^{-1}$; 3352, 1650, 1616, 1526, 1354,

NMR (DMSO—d$_6$) δ; 1.60(6H, s), 2.20-2.50, (2H, m), 2.65-2.98(4H, m), 5.75(1H, broad), 6.63(2H, d, J=8.9Hz), 7.44(2H, d, J=8.9Hz), 10.55(1H, s).

(4) Production of (2S)-(+)-1-(5-chloro-2-cyanophenoxy)-2,3-epoxypropane:

A mixed solution of 5.0 g of 5-chloro-2-cyano-phenol and 6.0 g of R-(—)-epichlorohydrin was heated at 120° C. for 2 hours under a nitrogen stream. Toluene (50 ml), 0.1 g of benzyl triethylammonium chloride and 20 ml of a 30% sodium hydroxide were added, and the mixture was stirred at room temperature for 2 hours. The organic layer was separated and dried over magnesium sulfate. The solvent was then evaporated. Ethanol was added to the residue to crystallize it. The crystals were then recrystrallized from ethyl acetate to give 2.4 g (2S)-(+)-(5-chloro-2-cyanophenoxy)-2,3-epoxypropane.
m.p. 85°-86° C.
[α]$_D^{20}$ +9.90 (C=1, C$_2$H$_5$OH)

(5) production of (2S)-6-[4-[2-[3-(5-chloro-2-cyanophenoxy)-2-hydroxypropylamino]-2-methylpropylamino]-phenyl]-4,5-dihydro-3(2H)-pyridazinone:

1.1 g of (2S)-(+)-1-(5-chloro-2-cyanophenoxy)-2,3-epoxypropane obtained in (4) above and 2.0 g of 6-[4-[2-amino-2-methylpropylamino]phenyl]-4,5-dihydro-3(2H)-pyridazinone were dissolved in 10 ml of isopropul alcohol, and the solution was heated with stirring for 20 hours under a nitrogen stream. The reaction solution was concentrated under reduced pressure. The residue was separated by silica gel chromatography (chloroform:methanol-20:1) to give 1.7 g of (2S)-6-[4-[2-[3-(5-chloro-2-cyanophenoxy)-2-hydroxypropylamino]-phenoxy]-4,5-dihydro-3(2H)-pyridazinone.
m.p. 156.5°-157.5° C.
[α]$_D^{20}$ +2.7 (C=1, DMF)
IR KBr cm$^{-1}$; 3345, 2228, 1654, 1614, 1358,
NMR (CDCl$_3$)δ; 1.20(6H, s), 2.30(1H, broad), 2.35-2.65(2H, m), 2.70-3.15(6H, m), 4.08(3H, m), 4.46(1H, broad), 6.59(2H, d, J=8.7Hz), 6.99(2H, m), 7.44(1H, d, J=8.7Hz), 7.52(2H, d, J=8.7Hz), 8.66(1H, broad).

(6) 1.44 g of (2S)-6-[2-[3-(5-chloro-2-cyanophenoxy)-2-hydroxypropylamino]-2-methylpropylamino]-phenoxy]-4,5-dihydro-3(2H)-pyridazinone was dissolved in ethanol, and the solution was added to an ethanol solution of 0.45 g of monoethylmaleic acid. The mixture was left to stand at room temperature. The crystal that precipitated were collected by filtration to obtain 1.14 g of the monoethylmaleate.
m.p. 153.5°-154.5° C.
[α]$_D^{25}$ —8.30 (C=1, CH$_3$OH)

In the same way as above, acids corresponding to the following salts were used instead of monoethylmaleic acid, the same compounds indicated below were obtained.

(7) Hydrochloride
m.p. 169.5°-171° C.
[α]$_D^{25}$ —9.31 (C=1, CH$_3$OH)
(8) Acetylglycine salt
m.p 135.5°-136° C.
[α]$_D^{25}$ —8.60 (C=1, CH$_3$OH)
(9) Fumarater
m.p. 218.5°-219.5° C.

EXAMPLE 2

6-[4-[2-[3-(5-chloro-2-cyanophenoxy)-2-hydroxypropylamino-2-methylpropylamino]phenyl]-4,5-dihydro-3(2H)-pyridazinone:

5.2 g of 6-[4-(2-amino-2-methylpropylamino)-phenyl]-4,5-dihydro-3(2H)-pyridazinone obtained in Example 1, (3) and 4.4 g of 1-(5-chloro-2-cyanophenoxy)-2,3-epoxypropane were dissolved in 30 ml of isopropyl alcohol, and the solution was heated with stirring for 20 hours. The solution was then worked up as in Example 1, (5) to give 8.2 g of 6-[4-[2-[3-(5-chloro-2-cyano-phenoxy)-2-hydroxypropylamino]-2-methylpropylamino]-pheyl]-4,5-dihydro-3(2H)-pyridazinone.
m.p. 160°-162° C.
IR KBr cm$^{-1}$; 3345, 2228, 1654, 1614, 1358,
NMR (CDCl$_3$)δ; 1.20(6H, s), 2.25(1H, broad), 2.35-2.65(2H, m), 2.70-3.15(6H, m), 4.09(3H, m), 4.46(1H, broad), 6.59(2H, d, J=8.7Hz), 6.99(2H, m), 7.44(1H, d, J=8.6Hz), 7.52(2H, d, J=8.7Hz), 8.60(1H, broad).

EXAMPLE 3

6-[4-[2-[3-(2,5-dichlorophenoxy)-2-hydroxypropylamino]-2-methylpropylamino]phenyl]-4,5-dihydro-3(2H)-pyridazinone:

2.3 g of 6-[4-(2-amino-2-methylpropylamino)-phenyl]-4,5-dihydro-3(2H)-pyridazinone obtained in Example 1, (3) and 1.6 g of 1-(2,5-dichlorophenoxy)-2,3-epoxypropane were dissolved in 20 ml of isopropyl alcohol, and heated with stirring for 24 hours. The solution was then worked up in the same way as in Example 1, (5). Recrystallization from dichloromethane-ether gave 2.35 g of 6-[4-[2-[3-(2,5-dichlorophenoxy)-2-hydroxypropylamino-2-methylpropylamino]phenyl]-4,5-dihydro-3(2H)-pyrdazinone.
m.p. 138.5°-139° C.
IR KBr cm$^{-1}$; 3395, 1618, 1360, 1266,
NMR (CDCl$_3$)δ; 1.19(6H, s), 2.35-2.70, (2H, m), 2.30(1H, broad), 2.70-3.10(4H, m), 3.03(2H, s), 4.05(3H, m), 4.45(1H, broad), 6.59(2H, d, J=8.9Hz), 6.8(2H, m), 7.24(1H, d, J=9.1Hz), 7.52(2H, d, J=8.9Hz), 8.68(1H, broad).

EXAMPLE 4

6-[4-[2-[3-(2-cyanophenoxy)-2-hydroxypropylamino]-2-methylpropylamino]phenyl]-4,5-dihydro-3(2H)-pyridazinone:

2.6 g of 6-[4-(2-amino-2-methylpropylamino)-phenyl]-4,5-dihydro-3(2H)-pyridazinone and 1.5 g of 1-(2-cyanophenoxy)-2,3-epoxypropane obtained in Example 1, (3) were dissolved in 20 ml of isopropanol, and heated with stirring for 24 hours. The solution was then worked up in the same way as in Example 1, (5). Recrystallization from dichloromethane-ether gave 2.93 g of 6-[4-[2-[3-(2-cyanophenoxy)-2-hydroxypropylamino]-2-methylpropyl-amino]phenyl]-4,5-dihydro-3(2H)-pyridazinone.
m.p. 126.0°-127.5° C.
IR KBr cm$^{-1}$; 3370, 2228, 1662, 1614, 1356,
NMR (CDCl$_3$)δ; 1.20(6H, s), 2.30(1H, broad), 2.35-2.65(2H, m), 2.70-3.15(6H, m), 4.08(3H, m), 4.51(1H, broad), 6.60(2H, d, J=8.8Hz), 7.01(2H, m), 7.50(2H, m), 7.52(2H, d, J=8.8Hz), 8.62(1H, broad).

EXAMPLE 5

6-[4-[2-[3-(3,4-dihydrocarbostyril-5-yloxy)-2-hydroxypropylamino]-2-methylpropylamino]phenyl]-4,5-dihydro-3(2H)-pyridazinone:

3.1 g of 6-[4-(2-amino-2-methylpropylamino)-phenyl]-4,5-dihydro-3(2H)-pyridazinone obtained in Example 1, (3) and 2.2 g of 1-(3,4-dihydrocarbostyril-5-yloxy)-2,3-epoxypropane were dissolved in 30 ml of isopropyl alcohol and heated with stirring for 20 hours. After the end of the reaction, the reaction solution was concentrated under reduced pressure. The residue was separated by silica gel chromatography (chloroform-methanol=10:1). Recrystallization from dichloromethane-isopropanol gave 2.4 g of 6-[4-[2-[3-(3,4-di hydrocarbostyril-5-yloxy)2-hydroxypropylamino]-2-methyl-propylamino]phenyl]-4,5-dihydro-3(2H)-pyridazinone.

m.p. 161°-162° C.

IR KBr cm$^{-1}$; 3369, 3250, 1677, 1648, 1347, 1207, 1102

NMR (CDCl$_3$)δ; 1.21(6H, s), 1.90(2H, broad), 2.35–2.70(4H, m), 2.70–3.10(8H, m), 3.99(1H, m), 4.03(2H, s), 4.45(1H, broad), 6.40(1H, m), 6.55(2H, d, J=8.7Hz), 7.10(1H, t, J=8.1Hz), 7.49(2H, d, J=8.7Hz), 7.70(2H, m), 8.52(1H, broad).

EXAMPLE 6

6-[4-[2-[3-(indol-4-yloxy)-2-hydroxypropyl-amino]-2-methylpropylamino]phenyl]-4,5-dihydro-3(2H)-pyridazinone:

Example 5 was repeated except that 1-(4-indol-yloxy)-2,3-epoxypropane was used instead of 1-(3,4-dihydrocarbostyril-5-yloxy)-2,3-epoxypropane. Thus, powdery 6-[4-[2-[3-(indol-4-yloxy)-2-hydroxypropylamino]--methylpropylamino]phenyl]-4,5-dihydro-3(2H)-pyridazinone was obtained.

IR KBr cm$^{-1}$; 1660, 1610(CO),

NMR (CDCl$_3$)δ; 1.21(6H, s), 1.68(3H, broad), 2.30–2.70(2H, m), 2.75–3.16(6H, m), 4.16(2H, broad), 4.30–4.65(1H, m), 6.43–6.70 (2H, m), 6.58(2H, d, J=9Hz), 6.95–7.17(3H, m), 7.53(2H, d, J=9Hz), 8.20(1H, broad), 8.36(1H, broad).

EXAMPLE 7

6-[4-[2-[3-(4-carbamoylmethylphenoxy)-2-hydroxy-propylamino]-2-methylamino]phenyl]-4,5-dihydro-3(2H)-pyridazinone:

Example 5 was repeated except that 1-(4-carbamoyl-methylphenoxy)-2,3-epoxypropane was used instead of 1-(3,4 dihydrocarbostyril-5-yloxy)-2,3-epoxypropane. Thus, powdery 6-[4-[2-[3-(4-(carbamoylmethylphenoxy)-2-hydroxypropylamino]-2-methylamino]phenyl]-4,5-dihydro-3(2H)-pyridazinone was obtained.

IR KBr cm$^{-1}$; 3338, 2964, 1664, 1612, 1511, 1347, 1245

NMR (CDCl$_3$)δ; 1.19(6H, s), 1.7(2H, broad), 2.55(2H, m), 2.70–3.10(6H, m), 3.51(2H, s), 3.96(1H, m), 3.99(2H, s), 4.50(1H, broad), 5.50(1H, broad), 6.58(2H, d, J=8.8Hz), 6.87(2H, d, J=9.0Hz), 7.14(2H, d, J=9.0Hz), 7.52(2H, d, J=8.8Hz).

EXAMPLE 8

6-[4-[2-(3-phenoxy-2-hydroxypropylamino)-2-methylpropylamino]phenyl]-4,5-dihydro-3(2H)-pyridazinone:

Example 5 was repeated except that 1-phenoxy-2,3-epoxypropane was used instead of 1-(3,4-dihydrocarbostyril-5-yloxy)-2,3-epoxypropane. 6-[4-[2-(3-phenoxy-2-hydroxypropylamino]-2-methyl-propylamino]-phenyl]-4,5-dihydro-3(2H)-pyridazinone was obtained.

m.p. 147°-148.5° C.

IR KBr cm$^{-1}$; 3370, 3284, 3197, 1655, 1609, 1351, 1240

NMR (CDCl$_3$)δ; 1.20(6H, s), 2.27(2H, broad), 2.53(2H, m), 2.70–3.10(6H, m), 3.98(1H, m), 4.01(2H, s), 4.55(1H, broad), 6.62(2H, d, J=9.0Hz), 6.90(3H, m), 7.25(2H, m), 7.53(2H, d, J=9.0Hz), 8.50(1H, broad).

EXAMPLE 9

6-[4-[2-[3-[4-(2-methoxyethyl)phenoxy]-2-hydroxy-propylamino]-2-methylpropylamino]phenyl]-4,5-dihydro-3(2H)-pyridazinone:

Example 5 was repeated except that 1-[4-(2-methoxyethyl)phenoxy]-2,3-epoxypropane was used instead of 1-(3,4-dihydrocarbostyril-5-yloxy)-2,3-epoxypropane. Thus, 6-[4-[2-[3-[4-(2-methoxyethyl)]phenoxy]-2-hydroxy-propylamino]-2-methylpropylamino]-phenyl]4,5-dihydro-3(2H)-pyridazinone was obtained.

m.p. 133.5°-135° C.

IR KBr cm$^{-1}$; 3335, 2865, 1646, 1609, 1510, 1354, 1255

NMR (CDCl$_3$)δ; 1.20(6H, s), 2.30(2H, broad), 2.54(2H, m), 2.70–3.10(8H, m), 3.34(3H, s), 3.56(2H, t, J=6.9Hz), 3.98(2H, s), 3.99(1H, m), 6.60(2H, d, J=9.0Hz), 6.82(2H, d, J=8.8Hz), 7.10(2H, d, J=8.8Hz), 7.53(2H, d, J=9.0Hz), 8.61(1H, broad).

Preparation Examples for the preparation of drugs containing the compounds of this invention will be given below.

Example A

Examples of recipes of tablets containing 5 mg and 20 mg of the active component per tablet are as follows:

|  | mg/tablet |
|---|---|
| Recipe 1-a. 5 mg tablet | |
| (2S)-6-[4-[2-[3-(5-chloro-2-cyanophenoxy)-2-hydroxypropylamino]-2-methylpropylamino]-phenyl]-4,5-dihydro-3(2H)-pyridazinone | 5 |
| Lactose | 137.2 |
| Starch | 44.8 |
| Carboxymethyl cellulose calcium | 10 |
| Talc | 2 |
| Magnesium stearate | 1 |
|  | 200.0 |
| Recipe 1-b. 20 mg tablet | |
| 6-[4-[2-[3-(5-chloro-2-cyanophenoxy)-2-hydroxypropylamino]-2-methylpropyl-amino]phenyl]-4,5-dihydro-3(2H)-pyridazinone | 20 |
| Lactose | 122.2 |
| Starch | 44.8 |
| Carboxymethyl cellulose calcium | 10 |
| Talc | 2 |
| Magnesium stearate | 1 |
|  | 200.0 |

The method of preparation in detail was as follows:

(2S) or 6-[4-[2-(2S)- 3-(5-chloro-2-cyanophenoxy)-2-hydroxypropylamino]-2 -methylpropylamino]-phenyl]-4,5-dihydro-3(2H)-pyridazinone or crystals of its optically active isomer were pulverized, and well mixed with lactose and starch. 10% of starch paste was added to the mixed powder, and stirred with stirring to produce granules. After drying, the granules were adjusted to about 840 microns, and talc and magnesium stearate were mixed, and the mixture was tableted.

| Example B: Injectable liquid | |
|---|---|
| (2S)-6-[4-[2-[3-(5-chloro-2-cyanophenoxy)-2-hydroxy-propylamino]-2-methylpropylamino]- | 5 mg |

| -continued |  |
|---|---|
| Example B: Injectable liquid |  |
| phenyl]-4,5-dihydro-3(2H)-pyridazinone |  |
| Macrogol 4000 | 20 mg |
| Polysorbate 20 | 4 mg |
| Sodium chloride | 9 mg |

Injectable distilled water to make 1 ml

The method of preparing the injectable preparation in detail was as follows:

Aseptically produced (2S)-6-[4-[2-[3-(5-chloro-2-cyanophenoxy)-2-hydroxypropylamino]2-methyl-propylamino]phenyl]-4,5-dihydro-3(2H)-pyridazinone was suspended in a solvent containing Macrogol 4000, polysorbate 20 and sodium chloride and sodium chloride in the amounts indicated above. After the pH of the suspension was adjusted to about 7.0, it was filled in ampoules and the ampoules were sealed by fusing.

We claim:

1. A pyridazinone compound of the formula

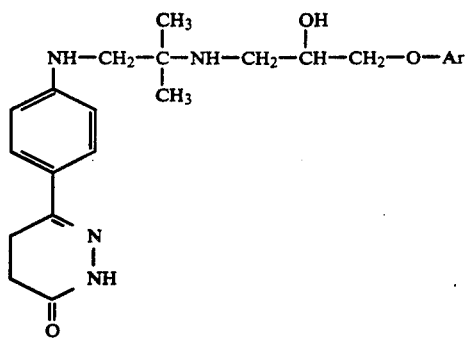

wherein Ar is

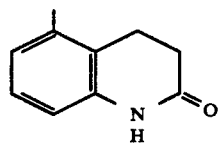

or a pharmaceutically acceptable salt thereof.

2. A pharmaceutical composition comprising an antihypertensively effective amount of the pyridazinone compound or its pharmaceutically acceptable salt as defined in claim 1 and a pharmaceutically acceptable carrier or diluent.

3. A method for treating a patient with hypertension, which comprises administering an antihypertensively effective amount of the pyridazinone compound or a pharmaceutically acceptable salt as defined in claim 1 to the patient.

* * * * *